United States Patent
Sanders

(10) Patent No.: US 6,427,544 B1
(45) Date of Patent: Aug. 6, 2002

(54) ENVIRONMENTALLY FRIENDLY ULTRA-HIGH SENSITIVITY LIQUID PENETRANT INSPECTION PROCESS AND SYSTEM

(75) Inventor: Stuart A. Sanders, Palm Beach Gardens, FL (US)

(73) Assignee: United Technologies Corporation, Hartford, CT (US)

( * ) Notice: Subject to any disclaimer, the term of this patent is extended or adjusted under 35 U.S.C. 154(b) by 7 days.

(21) Appl. No.: 09/805,863

(22) Filed: Mar. 14, 2001

(51) Int. Cl.$^7$ .................. G01M 19/00; G01T 1/61
(52) U.S. Cl. .................. 73/865.8; 250/302
(58) Field of Search .................. 73/865.8; 250/302; 252/301.19

(56) References Cited

U.S. PATENT DOCUMENTS 3,735,131 A * 5/1973 Sherwin .................. 250/302
3,965,350 A * 6/1976 Molina .................. 250/302
4,331,871 A * 5/1982 Allinikov .................. 250/302
4,377,492 A * 3/1983 Jones .................. 252/301.19
4,621,193 A * 11/1986 Van Hoye .................. 250/302

* cited by examiner

*Primary Examiner*—Hezron Williams
*Assistant Examiner*—Jay L Politzer
(74) *Attorney, Agent, or Firm*—Bachman & LaPointe, P.C.

(57) ABSTRACT

The present invention relates to a process for inspecting a part to detect defects in the part. The process comprises the steps of placing a part to be inspected in an immersion tank, introducing a mixture of a penetrant dye and a supercritical carbon dioxide solvent into the immersion tank, maintaining the part immersed in the mixture for a time sufficient for the penetrant dye to penetrate any defects in the part, removing the part from the immersion tank, and inspecting the part for the presence of any defects. A system for carrying out the process is also described.

20 Claims, 1 Drawing Sheet

6,427,544 B1

ENVIRONMENTALLY FRIENDLY ULTRA-HIGH SENSITIVITY LIQUID PENETRANT INSPECTION PROCESS AND SYSTEM

BACKGROUND OF THE INVENTION

The present invention relates to an improved process for inspecting parts which offers higher sensitivity and lower environmental toxicity and to a system for carrying out the inspection process.

Liquid penetrant inspection of parts has been used in numerous industries for decades to identify both manufactured defects and in-service damage, such as cracks, which might lead to catastrophic failure of the part under continued use. In a typical process, a clean part is immersed in a penetrant solution which migrates into any features of the part open to the surface, such as cracks, porous surfaces, etc. The part is removed from the solution, drained and wiped to remove the penetrant from the surface, leaving only that penetrant which migrated into the features of interest. A developer is then applied to bring out the trapped penetrant, and the part is examined under the appropriate light conditions such as visible if dye penetrant or ultraviolet if fluorescent. Defects are indicated by the penetrant.

One of the major factors which determines the sensitivity, i.e. ability to highlight smaller cracks and defects, of this process is the ability of the penetrant solution to seep into the features of interest. In conventional organic solvent-based systems, this ability is afforded by a combination of low viscosity and high surface tension of the solvent, which allow it to migrate into tight cracks through capillary action. Suitable solvents generally include alcohols, ethers, ketones, esters, and chlorinated hydrocarbons. Unfortunately, many of these substances, particularly the chlorinated hydrocarbons, are harmful to both people and the environment, resulting in higher costs due to protective measures/training for operators as well as hazardous waste management and disposal. If the parts being inspected are large, requiring large volumes of penetrant, these costs can be significant.

Supercritical fluid technology has been used for years in extraction processes in the food, cosmetics, and petroleum industries. Supercritical fluids offer an attractive alternative to industrial hydrocarbon and chlorofluorocarbon solvents due to their low environmental impact, high volatility, low viscosity and high solvating power in the supercritical state. Recently, this technology has made significant inroads in the precision cleaning, less than 10 micrograms of contaminant per square centimeter of surface, industry for most of the same reasons. Perhaps the most widely used of the fluids is carbon dioxide, known as $SCCO_2$ in its supercritical state, because its critical temperature and pressure, 88° F. and 1070 psi respectively, are easily handled by conventional process equipment and construction materials. A typical $SCCO_2$ cleaning facility is represented in FIG. 1. As shown therein, the facility includes a liquid carbon dioxide storage tank 10, a pump 12 for transporting the liquid carbon dioxide and raising the pressure of the liquid carbon dioxide, a heater 14 for raising the temperature of the liquid carbon dioxide to a critical temperature at which it becomes supercritical carbon dioxide, a cleaning tank 16 to which the supercritical carbon dioxide is fed, a separator 18 for removing impurities and contaminants from the supercritical carbon dioxide being recycled, and a cooler 20 for lowering the temperature of the recycled supercritical carbon dioxide to convert it into a liquid, non-supercritical state. The ability to cycle between the supercritical state in the cleaning tank 16 and a subcritical state, i.e. gas-phase, in the separator 18 allows for efficient extraction of impurities and contaminants from the supercritical carbon dioxide. In the context of a cleaning system, it also facilitates any removal of the cleaning solvent. Not only does this minimize the up-front cleaning solvent cost, but also minimizes the waste generated and thus the treatment/disposal cost.

SUMMARY OF THE INVENTION

It is an object of the present invention to provide an improved process for inspecting a part for defects.

It is a further object of the present invention to provide a process as above which uses supercritical carbon dioxide ($SCCO_2$) as the solvent phase in a liquid penetrant inspection process.

It is yet another object of the present invention to provide a system for carrying out the inspection process of the present invention.

The foregoing objects are attained by the process and the system of the present invention.

In accordance with the present invention, a process for inspecting a part to detect defects broadly comprises the steps of placing a part to be inspected in an immersion tank, introducing a mixture of a penetrant dye and a supercritical carbon dioxide solvent into the immersion tank, maintaining the part immersed in the mixture for a time sufficient for the penetrant dye to penetrate any defects in the part, removing the part from the immersion tank, and inspecting the part for the presence of any defects.

A system in accordance with the present invention broadly comprises means for forming a mixture of a penetrant dye and a supercritical carbon dioxide solvent, means for immersing a part to be inspected into the mixture for a time period sufficient to allow the penetrant dye and the supercritical carbon dioxide to penetrate defects in the part, and means for inspecting the part after removal of the part from the immersing means to detect the presence of any defects.

Other details of the process and system of the present invention, as well as other objects and advantages attendant thereto, are set forth in the following description and the accompanying drawings wherein like reference numerals depict like elements.

DETAILED DESCRIPTION OF THE PREFERRED EMBODIMENT(S)

Figure 1:
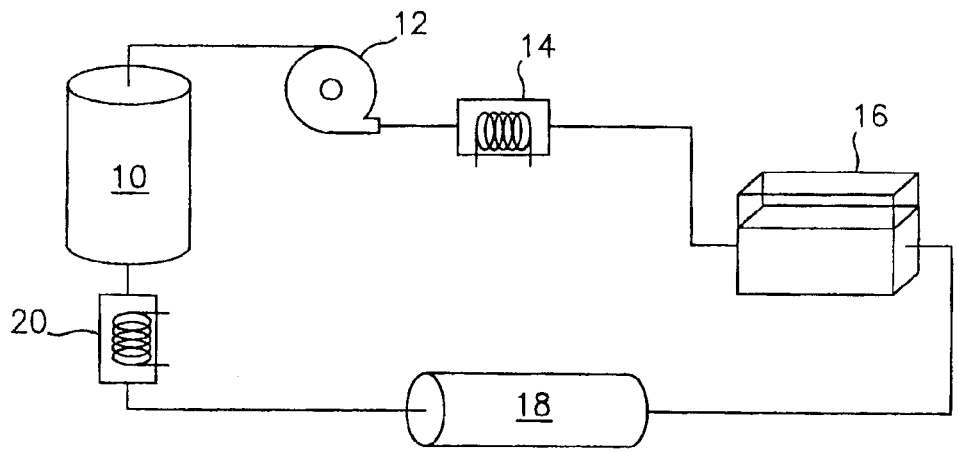
FIG. 1 is a schematic representation of a prior art supercritical carbon dioxide cleaning facility.
Figure 2:
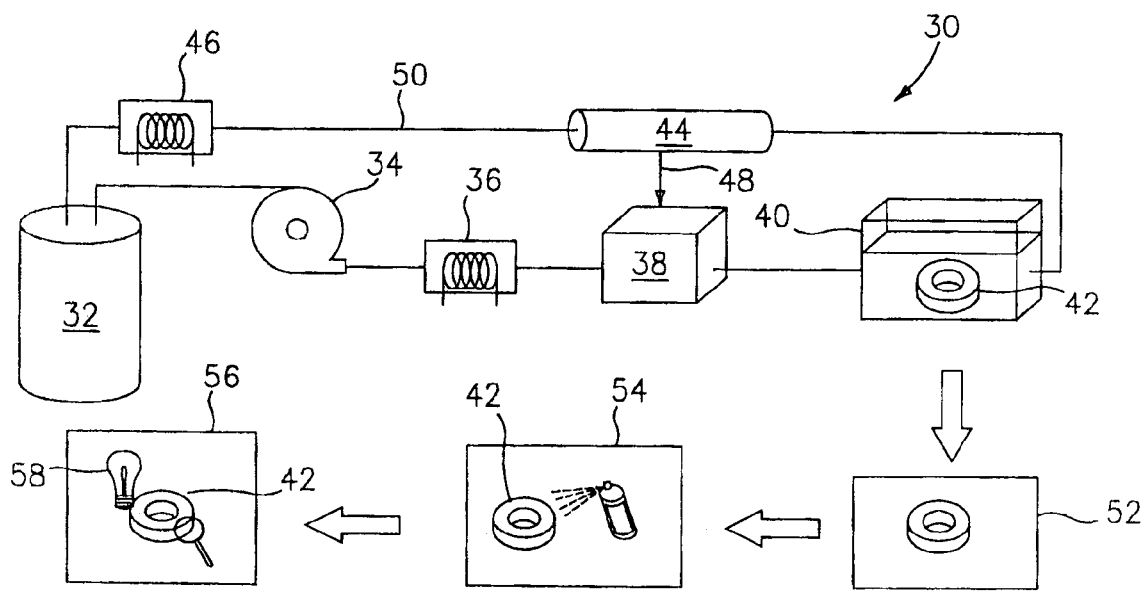
FIG. 2 is a schematic representation of an inspection system in accordance with the present invention.

Referring now to FIG. 2, a system 30 for performing an inspection process for detecting defects in accordance with the present invention is illustrated. The system 30 includes a liquid storage tank 32 for holding liquid carbon dioxide and a pump 34 for creating a flow of the liquid carbon dioxide and for increasing the pressure of the liquid carbon dioxide. The pump 34 increases the pressure to a pressure above 1070 psi. The facility 30 also has a heater 36 for elevating the temperature of the liquid carbon dioxide to a temperature above 88° F. Both pressure and temperature must be maintained above these values to keep the carbon dioxide in a supercritical state. Variations in temperature and pressure above the critical point may be employed to effect changes in the density of the supercritical carbon dioxide, which in turn will have a direct impact on the ability of the $CO_2$ to dissolve the penetrant compound of choice. In general, the higher the $CO_2$ density in the supercritical range, the higher its solvating capacity.

The supercritical carbon dioxide is then passed to a mixing tank 38, where it is mixed with a penetrant dye. The penetrant dye may comprise any suitable penetrant dye known in the art. For example, the penetrant dye may be an organic or inorganic composition. It may also be visible or fluorescent type. If fluorescent type, the penetrant dye preferably should have an excitation wavelength of at least 320 nm and most preferably an emission wavelength greater than 440 nm. The penetrant dye may be liquid or solid phase. If solid, the dye needs to retain sufficient mobility to be drawn out of a flaw when a developer is applied. If needed, a mobilizing agent may be added to the penetrant dye. This could be done by predissolving the dye in a secondary solvent which would remain after the $CO_2$ reverts to a gaseous state under subcritical conditions. This method may be preferred with water soluble dyes. Alternatively, a secondary solvent could be spray applied directly to the part after the $CO_2$ has been removed and the excess dye has been removed from the part surface, but prior to the application of any developer. If liquid, the penetrant dye should have a relatively low viscosity to remain mobile, preferably less than 1 centipoise. The use of a liquid dye may impose restrictions on how fast the $CO_2$ is allowed to off-gas at subcritical conditions to prevent forced ejection of the dye from a flaw space. The penetrant dye which is mixed with the supercritical carbon dioxide should have high solubility in carbon dioxide. The concentration of the penetrant dye in the supercritical carbon dioxide solvent is a function of $CO_2$ density.

The system 30 has an immersion tank 40. The immersion tank may be formed from any suitable material known in the art. The part 42 to be inspected is placed in the immersion tank 40 and the tank 40 is sealed prior to introducing the penetrant dye-supercritical carbon dioxide mixture into the tank 40. After the penetrant dye-supercritical carbon dioxide mixture has been introduced into the tank 40, the part 42 resides in the tank 40 for a time sufficient to allow the mixture to penetrate any defects in the part 42.

Prior to removing the part 42 from the tank 40, the penetrant dye-supercritical carbon dioxide mixture is removed from the tank 40. Any suitable means known in the art, such as a gravity drain, may be used to remove the mixture from the tank 40. The mixture may then be sent to a separator 44 wherein the penetrant dye is separated from the supercritical carbon dioxide. The separator 44 may comprise any suitable separating device known in the art. After separation, the penetrant dye may be recycled and reintroduced into the mixing tank 38 via line 48. The separated supercritical carbon dioxide may then flow via line 50 to cooler 46 where the temperature is lowered so that the carbon dioxide is in a liquid, non-supercritical state. The liquid, non-supercritical liquid carbon dioxide may then be returned to the storage tank 32.

Where there is no desire to recycle the used penetrant dye and/or the carbon dioxide, the separator 44 and the cooler 46 may be omitted.

After removal of the part 42 from the tank, the supercritical carbon dioxide solvent which has penetrated the defects in the part along with the penetrant dye will go to a gaseous state. The system 30 includes a wiping and drying station 52. In the station 52, the outer surfaces of the part 42 are wiped to remove any excess penetrant dye residue. After wiping, the part is dried using any suitable technique known in the art.

The clean and dried part 42 is then transferred to a developing station 54. In the developing station 54, a developer is applied to the part 42 to bring the trapped penetrant dye to the surface of the part so that the defects can be seen. Any suitable developer known in the art may be used to bring out the penetrant dye. A particularly useful developer is one which combines the functions of mobilizer and developer.

From the developing station 54, the part 42 is transferred to an inspection station 56. In the inspection station 56, the part 42 is placed under a monochromatic light source 58, such as visible light or ultraviolet light if the penetrating dye is a fluorescing dye, to detect any defects in the part 42.

The process of the present invention provides several advantages over current penetrant methods. First, the process provides higher defect sensitivity due to the increased penetrating power of supercritical carbon dioxide over organic solvents. Second, the process has a lower operating cost due to the minimization of hazardous waste streams, operator protection and training, and lower raw material cost. Third, the process has a lower environmental risk. Fourth, the process is easy to implement.

It is apparent that there has been provided in accordance with the present invention an environmental friendly ultra-high sensitivity liquid penetration inspection process and system which fully satisfy the objects, means, and advantages set forth hereinbefore. While the present invention has been described in the context of specific embodiments thereof, other alternatives, modifications, and variations will become apparent to those skilled in the art having read the foregoing description. Therefore, it is intended to embrace those alternatives, modifications and variations which fall within the broad scope of the appended claims.

What is claimed is:

1. A process for inspecting a part to detect defects comprising the steps of:

placing a part to be inspected in an immersion tank;

introducing a mixture of a penetrant dye and a supercritical carbon dioxide solvent into said immersion tank;

maintaining said part immersed in said mixture for a time sufficient for said penetrant dye and supercritical carbon dioxide to penetrate any defects in said part;

removing said part from said immersion tank; and inspecting said part for the presence of any defects.

2. A process according to claim 1, further comprising sealing said tank prior to introducing said mixture.

3. A process according to claim 1, wherein said introducing step comprises introducing a mixture of a fluorescing penetrant dye and said supercritical carbon dioxide solvent into said tank.

4. A process according to claim 1, further comprising allowing said supercritical carbon dioxide solvent in any defect to convert to a gaseous state after said removing step, wiping outer surfaces of said part to remove penetrant dye residue, and drying said part.

5. A process according to claim 4, further comprising applying a developer to said part after said wiping and drying steps to raise said penetrant dye in any defect.

6. A process according to claim 5, wherein said inspecting step comprises placing said part under a monochromatic light to detect the presence of said penetrant dye in any defect.

7. A process according to claim 1, further comprising providing a source of liquid carbon dioxide, and passing said liquid carbon dioxide through a pump to raise the pressure of said liquid carbon dioxide and through a heater to raise the temperature of said liquid carbon dioxide to a level which converts the liquid carbon dioxide to a supercritical carbon dioxide state prior to said introducing step.

8. A process according to claim 7, further comprising. prior to said mixture introducing step, introducing said supercritical carbon dioxide into a mixing tank and adding a penetrant dye to said supercritical carbon dioxide in said mixing tank to form said mixture.

9. A process according to claim 8, wherein said penetrant dye adding step comprising adding a fluorescing penetrant dye.

10. A process according to claim 8, further comprising removing said penetrant dye—supercritical carbon dioxide mixture from said immersion tank prior to removing said part and transporting said mixture to a separator to separate said penetrant dye from said supercritical liquid carbon dioxide.

11. A process according to claim 10, further comprising recycling said removed penetrant dye to said mixing tank and recycling said separated supercritical carbon dioxide to said source.

12. A process according to claim 11, further comprising passing said separated supercritical carbon dioxide through a cooler to convert said supercritical carbon dioxide to liquid carbon dioxide before introducing said liquid carbon dioxide into said source.

13. A system for inspecting parts for defects comprising:
means for forming a mixture of a penetrant dye and a supercritical carbon dioxide solvent;
means for immersing a part to be inspected into said mixture for a time period sufficient to allow said penetrant dye and said supercritical carbon dioxide to penetrate defects in said part; and
means for inspecting said part after removal of said part from said immersing means to detect the presence of any defects.

14. A system according to claim 13, wherein said forming means comprises a source of liquid carbon dioxide, a pump for elevating the pressure of said liquid carbon dioxide, and a heater for raising the temperature of said liquid carbon dioxide to a level where said liquid carbon dioxide becomes supercritical carbon dioxide.

15. A system according to claim 14, wherein said forming means further comprises a mixing tank for adding said penetrant dye to said supercritical carbon dioxide.

16. A system according to claim 13, wherein immersing means comprises a sealed immersion tank.

17. A system according to claim 13, wherein said inspecting means comprises a first station for wiping and drying the part after removal of said part from said immersing means, a second station for applying a developer to said part to raise the penetrant dye in any defect, and a third station for placing said part under a source of monochromatic light to detect said raised penetrant dye in said any defect.

18. A system according to claim 13, further comprising means for recycling said penetrant dye and said supercritical carbon dioxide in said mixture.

19. A system according to claim 18, wherein said recycling means includes a separator for separating said recycled penetrant dye from said recycled supercritical carbon dioxide.

20. A system according to claim 18, wherein said recycling means further comprises means for delivering said recycled penetrant dye to said forming means and a cooler for converting said recycled supercritical carbon dioxide to liquid carbon dioxide.

* * * * *